United States Patent
Ozawa et al.

(10) Patent No.: US 9,521,986 B2
(45) Date of Patent: Dec. 20, 2016

(54) PORTABLE RADIOGRAPHIC IMAGING SYSTEM

(71) Applicant: Konica Minolta, Inc., Tokyo (JP)

(72) Inventors: Kenichi Ozawa, Tokyo (JP); Masahiro Kojima, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 137 days.

(21) Appl. No.: 14/485,090

(22) Filed: Sep. 12, 2014

(65) Prior Publication Data

US 2015/0078521 A1    Mar. 19, 2015

(30) Foreign Application Priority Data

Sep. 13, 2013  (JP) ................. 2013-190392

(51) Int. Cl.
*A61B 6/00* (2006.01)

(52) U.S. Cl.
CPC ............ *A61B 6/542* (2013.01); *A61B 6/4233* (2013.01); *A61B 6/4266* (2013.01); *A61B 6/4283* (2013.01); *A61B 6/4405* (2013.01); *A61B 6/54* (2013.01); *A61B 6/548* (2013.01); *A61B 6/563* (2013.01); *A61B 6/566* (2013.01); *A61B 6/56* (2013.01)

(58) Field of Classification Search
CPC ... A61B 6/4208; A61B 6/4233; A61B 6/4266; A61B 6/4283; A61B 6/4405; A61B 6/54; A61B 6/548; A61B 6/56; A61B 6/563; A61B 6/566
USPC ........... 378/97, 98.8, 108–110, 114, 115, 91; 250/370.09
See application file for complete search history.

(56) References Cited

U.S. PATENT DOCUMENTS

| | | | | |
|---|---|---|---|---|
| 5,661,309 A | * | 8/1997 | Jeromin ............... | G03G 15/758 250/370.09 |
| 7,015,478 B2 | * | 3/2006 | Yamamoto ............... | A61B 6/00 250/370.09 |
| 7,545,914 B2 | * | 6/2009 | Kito ..................... | A61B 6/4283 378/207 |
| 7,696,484 B2 | * | 4/2010 | Yokoyama ............... | A61B 6/00 250/370.09 |
| 7,737,427 B2 | * | 6/2010 | Kito ..................... | A61B 6/4233 250/370.08 |
| 7,787,594 B2 | * | 8/2010 | Ohta .................... | A61B 6/4233 378/114 |

(Continued)

FOREIGN PATENT DOCUMENTS

| | | |
|---|---|---|
| JP | 06342099 A | 12/1994 |
| JP | 2012105787 A | 6/2012 |

(Continued)

*Primary Examiner* — Allen C. Ho
(74) *Attorney, Agent, or Firm* — Cantor Colburn LLP

(57) ABSTRACT

A portable radiographic imaging system includes an FPD cassette and a portable console, each of which is configured to wirelessly communicate with a portable relay unit. The relay unit prohibits a radiation generator from emitting radiation when judging that a wireless communication connection has not been established between the relay unit and the radiation generator, and allows the radiation generator to emit radiation when judging that the wireless communication connection has not been established between the relay unit and the radiation generator after an interlock release signal is transferred from the console or the like to the radiation generator.

6 Claims, 5 Drawing Sheets

(56) References Cited

U.S. PATENT DOCUMENTS

| | | | | |
|---|---|---|---|---|
| 7,896,547 B2* | 3/2011 | Kito | A61B 6/4283 378/205 |
| 7,991,119 B2* | 8/2011 | Yoshida | G01T 1/00 378/114 |
| 8,080,802 B2* | 12/2011 | Nishino | A61B 6/4233 250/370.08 |
| 8,130,909 B2* | 3/2012 | Nishino | A61B 6/4283 250/370.09 |
| 8,174,358 B2* | 5/2012 | Butzine | A61B 6/544 340/12.22 |
| 8,203,446 B2* | 6/2012 | Tsubota | H04W 48/02 340/539.1 |
| 8,243,882 B2* | 8/2012 | Jabri | A61B 6/4411 378/116 |
| 8,265,225 B2* | 9/2012 | Nishino | A61B 6/4283 378/102 |
| 8,295,439 B2* | 10/2012 | Yonekawa | A61B 6/00 378/115 |
| 8,330,597 B2* | 12/2012 | Nishino | A61B 6/00 250/370.01 |
| 8,331,530 B2* | 12/2012 | Butzine | A61B 6/4405 378/204 |
| 8,334,515 B2* | 12/2012 | Tsubota | A61B 6/548 250/370.08 |
| 8,334,516 B2* | 12/2012 | Tsubota | A61B 6/4283 250/370.08 |
| 8,345,820 B2* | 1/2013 | Yoshida | G03B 42/04 250/370.09 |
| 8,357,908 B2* | 1/2013 | Kuwabara | A61B 6/56 250/370.08 |
| 8,358,740 B2* | 1/2013 | Nakatsugawa | A61B 6/102 378/116 |
| 8,363,786 B2* | 1/2013 | Nakatsugawa | A61B 6/4441 378/116 |
| 8,401,150 B2* | 3/2013 | Watanabe | A61B 6/4283 378/114 |
| 8,461,544 B2* | 6/2013 | Iwakiri | G03B 42/04 250/370.09 |
| 8,523,433 B2* | 9/2013 | Butzine | A61B 6/4405 378/115 |
| 8,532,262 B2* | 9/2013 | Iwakiri | A61B 6/4233 250/370.09 |
| 8,546,777 B2* | 10/2013 | Utsunomiya | A61B 6/4283 250/580 |
| 8,678,649 B2* | 3/2014 | Bechard | A61B 6/00 378/198 |
| 8,768,035 B2* | 7/2014 | Liu | A61B 6/585 378/62 |
| 8,855,691 B2* | 10/2014 | Kamiya | A61B 6/4283 340/2.1 |
| 8,899,831 B2* | 12/2014 | Yoshida | A61B 6/4233 250/370.08 |
| 8,923,482 B2* | 12/2014 | Tajima | H05G 1/44 378/108 |
| 8,956,045 B2* | 2/2015 | Tajima | A61B 6/4283 378/145 |
| 8,971,494 B2* | 3/2015 | Tajima | A61B 6/542 378/108 |
| 8,983,035 B2* | 3/2015 | Noma | H05G 1/64 250/214 DC |
| 9,042,519 B2* | 5/2015 | Kuwabara | A61B 6/4283 378/114 |
| 9,044,191 B2* | 6/2015 | Nishino | A61B 6/4405 |
| 9,055,922 B2* | 6/2015 | Kuwabara | A61B 6/542 |
| 9,060,731 B2* | 6/2015 | Kuwabara | A61B 6/4233 |
| 9,060,738 B2* | 6/2015 | Kuwabara | A61B 6/542 |
| 9,101,328 B2* | 8/2015 | Tsuji | G01T 1/026 |
| 9,117,289 B2* | 8/2015 | Matsumoto | A61B 6/50 |
| 9,146,326 B2* | 9/2015 | Kuwabara | G01T 1/17 |
| 9,168,016 B2* | 10/2015 | Ohta | G01T 1/24 |
| 9,232,620 B2* | 1/2016 | Tajima | H05G 1/42 |
| 9,265,467 B2* | 2/2016 | Kamiya | A61B 6/5241 |
| 9,282,943 B2* | 3/2016 | Oda | A61B 6/5258 |
| 9,326,745 B2* | 5/2016 | Muraoka | A61B 6/5217 |
| 9,351,699 B2* | 5/2016 | Kuwabara | A61B 6/542 |

FOREIGN PATENT DOCUMENTS

| | | |
|---|---|---|
| JP | 2013111198 A | 6/2013 |
| WO | 2006101233 A1 | 9/2006 |

* cited by examiner

PORTABLE RADIOGRAPHIC IMAGING SYSTEM

CROSS-REFERENCE TO RELATED APPLICATION

The present invention claims priority under 35 U.S.C. §119 to Japanese Application No. 2013-190392 filed Sep. 13, 2013, the entire content of which is incorporated herein by reference.

BACKGROUND OF THE INVENTION

Field of the Invention

The present invention relates to a portable radiographic imaging system, especially to a portable radiographic imaging system which performs radiographic imaging using an FPD cassette, etc.

Description of Related Art

In the field of radiographic imaging, an imaging method has changed from an analog system to a digital system with the transition from a conventional silver salt photography method using a screen/film to a method using a computed radiography (CR) cassette, a photostimulable phosphor sheet, etc. Recently, various kinds of Flat Panel Detectors (hereinafter referred to as "FPDs"; also called as "radiographic image capturing apparatuses" or the like) has been developed, in which conversion elements are two-dimensionally arranged, each of the elements generating electrical signals depending on radiation that has been emitted from a radiation source and has passed through an object. Such FPDs have come into use in medical image photographing in a medical front such as a hospital.

In recent years, a portable FPD (hereinafter referred to as "FDP cassette") which houses in a casing a sensor panel including the above-mentioned conversion elements formed thereon so that it becomes portable has been developed and put to practical use (for example, see Japanese Patent Application Laid-Open Publication No. H06-342099). There has also been developed a radiographic imaging system in which signals, data, etc. are transmitted/received in wireless communication among an FPD cassette, a radiation generator that emits radiation to the FPD cassette, and a console that generates radiographic images based on image data taken by the FPD cassette (for example, see Japanese Patent Application Laid-Open Publication No. 2013-111198).

When performing wireless communication among the console, the FPD cassette, etc., if the radiation generator emits radiation to the FPD cassette through an object in the state that wireless communication connection has not been established, there is a possibility that radiation generator emits radiation to the FPD cassette which has not completed preprocessing for imaging yet.

In this regard, for example, WO2006/101233 discloses the configuration where the radiation generator does not emit radiation when the wireless communication connection has not been established between the console and the FPD cassette.

Meanwhile, for example, Japanese Patent Application Laid-Open Publication No. 2013-111198 discloses that, in the case of configuration where signals, data, etc. are transmitted/received in wireless communication among the FPD cassette, the radiation generator, and the console (and further a key unit in Japanese Patent Application Laid-Open Publication No. 2013-111198), wireless communication is performed between the FPD cassette and the radiation generator, between the FPD cassette and the console, and between the radiation generator and the console (and further between the key unit and each of the devices in the case of providing the key unit).

In such case, however, when replacing the console of the system with another console, and/or when incorporating new additional FPD cassette into the system, setting or the like is necessary to establish new wireless communication between the new device, which has been replaced or incorporated into the system, and each of the other devices of the system.

Concretely, it is necessary for the new device, which has been replaced or incorporated into the system, to set identification information (for example, SSID in the case of wireless communication by wireless Local Area Network (LAN)) etc. of all other devices of the system in order to execute wireless communication with the other devices. At the same time, it is also necessary for each of the other devices of the system to set identification information etc. of the new device, which has been replaced or incorporated into the system, to wirelessly communicate with the new device.

The processing to enable wireless communication among the devices of the system, when replacing the device of the system or incorporating the new device into the system, is complicated and troublesome for a radiologist or the like, which has been a problem.

In the meantime, by making the above-mentioned FPD cassette, the radiation generator, the console, etc. portable, the whole radiographic imaging system can be made portable. When making the radiographic imaging system portable, for example, a patient who cannot come to facilities such as a hospital equipped with imaging facility can bring the portable radiographic imaging system into his/her home so as to perform radiographic imaging at his/her home.

Moreover, it also becomes possible to bring the portable radiographic imaging system into an imaging location to perform radiographic imaging in the case that a farm animal such as a cow and/or an animal such as a racehorse breaks a bone, and/or in the case of performing radiographic imaging of teeth of a dead body for identification in time of disaster. Thus, by making the radiographic imaging system portable, the system can be brought into not only facilities such as a hospital, but also various locations, so that radiographic imaging is performed there.

When bringing the portable system into the imaging location, for example, there may be a situation where communication environment is deteriorated due to wireless communication established among various apparatuses/devices other than the portable system in the imaging location, and accordingly wireless communication connection among the console, the FPD cassette, the radiation generator, etc. of the portable system is disconnected, namely, wireless communication connection is not established in the portable system.

Moreover, when a plurality of portable radiographic imaging systems are brought into an imaging location for a body identification or the like, there may be a situation where radio waves used in wireless communication of the plural systems fly about in one (1) imaging location, which is so-called busy state of communication. In such a state, there may be a case that it takes time for each device to perform processing to judge whether or not received signals, data, etc. are those that are to be transmitted to the device itself, in order to avoid confusion, and thereby it takes extra time for the device to perform communication. There also may be a case that it takes quite a long time to confirm absence/presence of wireless communication that has wrongly entered due to confusion, the processing time exceeds the upper limit time predetermined for original routine processing and time out error processing is performed, and accordingly wireless communication connection among the devices of the same system is temporarily disconnected.

In such a state, as described in above-mentioned WO2006/101233, if the radiation generator is controlled so as not to emit radiation to the FPD cassette when wireless communication connection has not been established among the devices of the system, even when the FPD cassette has completed preprocessing for imaging and in the state capable of being irradiated with radiation, the radiation generator does not emit radiation if wireless communication connection is disconnected.

In the above case, radiographic imaging is not performed in the result though both of the FPD cassette and the radiation generator are ready for radiographic imaging, and thereby a good opportunity for imaging is missed. Moreover, the FPD cassette is required to execute preprocessing for imaging again, and power of a built-in battery is wastefully consumed.

However, if the radiation generator emits radiation to the FPD cassette, even when wireless communication connection among the devices of the system is disconnected, in order to prevent the above situation from occurring, there may be a situation where the radiation generator emits radiation to the FPD cassette which has not completed the preprocessing for imaging.

Therefore, imaging becomes necessary again, and radiation irradiation is wasted in the result. Accordingly, power of the built-in battery of the FPD cassette is wastefully consumed.

SUMMARY OF THE INVENTION

The present invention is made in view of the foregoing problems, and an object of the present invention is to provide a portable radiographic imaging system in which the devices thereof can easily execute wireless communication with one another even in the case of replacing the device of the system or incorporating a new device into the system. The portable radiographic imaging system can accurately perform imaging even in the case that wireless communication connection among the devices thereof is disconnected, and can accurately prohibit the radiation generator from emitting radiation when imaging may not be performed accurately.

In order to achieve the above object, according to one aspect of the present invention, there is provided a portable radiographic imaging system which includes an FPD cassette and a portable console, the system including: a portable relay unit which performs wireless communication with a portable radiation generator emitting radiation to an object, wherein each of the FPD cassette and the console is configured to perform wireless communication with the relay unit, and the relay unit prohibits the radiation generator from emitting radiation when judging that a wireless communication connection has not been established between the relay unit and the radiation generator, and allows the radiation generator to emit radiation when judging that the wireless communication connection has not been established between the relay unit and the radiation generator after the relay unit transfers to the radiation generator a signal to allow the radiation generator to emit radiation, the signal being sent from the FPD cassette or the console.

BRIEF DESCRIPTION OF THE DRAWINGS

The present invention will become more fully understood from the detailed description given hereinbelow and the appended drawings, and thus are not intended as a definition of the limits of the present invention, and wherein.

DESCRIPTION OF EMBODIMENTS

Hereinafter, an embodiment of a portable radiographic imaging system according to the present invention will be described with reference to the drawings.

Figure 1:
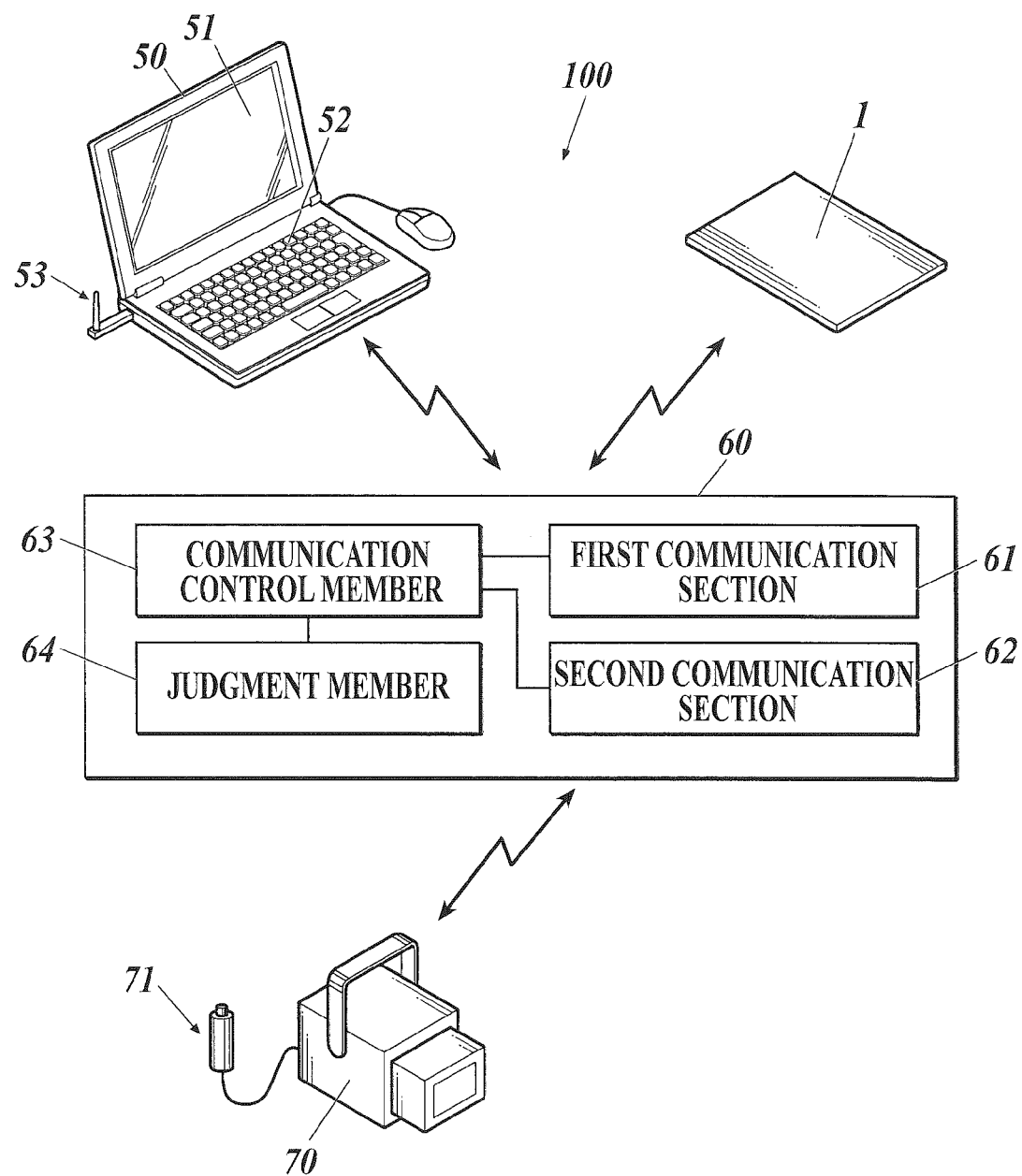
FIG. 1 is an overall view of a portable radiographic imaging system according to this embodiment.

FIG. 1 is an overall view of a portable radiographic imaging system according to this embodiment. In the embodiment, the portable radiographic imaging system 100 includes at least an FPD cassette 1, a portable console 50, and a portable relay unit 60. Each of the FPD cassette 1 and the console 50 is configured to wirelessly communicate with the relay unit 60.

Hereinafter, the devices constituting the portable radiographic imaging system 100 of the embodiment will be described.

Incidentally, FIG. 1 illustrates the example where each of the console 50, the relay unit 60 and a radiation generator 70 is an independent portable device, and they constitute the portable radiographic imaging system 100 together. However, the present invention can also be applied to the case that these devices are mounted on one (1) non-illustrated wagon so that they are assembled in a shape of a so-called mobile X-ray imaging cart.

[FPD Cassette 1]

Figure 2:
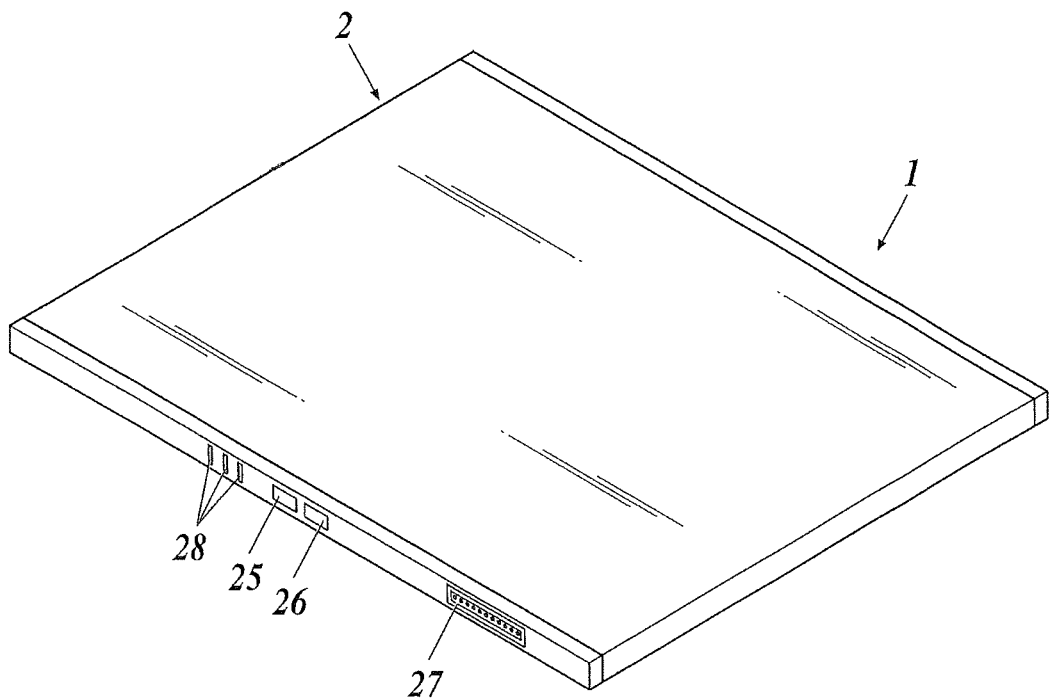
FIG. 2 is a perspective view illustrating an exterior appearance of an FPD cassette.

FIG. 2 is a perspective view illustrating the exterior appearance of the FPD cassette. In the embodiment, the FPD cassette 1 is made by housing a non-illustrated sensor panel in a casing 2 composed of carbon plates. On one side of the casing 2, a power switch 25, a selector switch 26, a connector 27, an indicator 28, etc. are disposed.

Moreover, though non-illustrated, an antenna device 29 (see FIG. 3 to be described later) which enables wireless communication with outside apparatuses/devices is disposed, for example, on another side of the casing 2, in the embodiment. Incidentally, in the embodiment, the FPD cassette 1 has the configuration in which a non-illustrated cable is inserted into the connector 27 in the case of executing wire communication with external apparatuses/devices.

Figure 3:
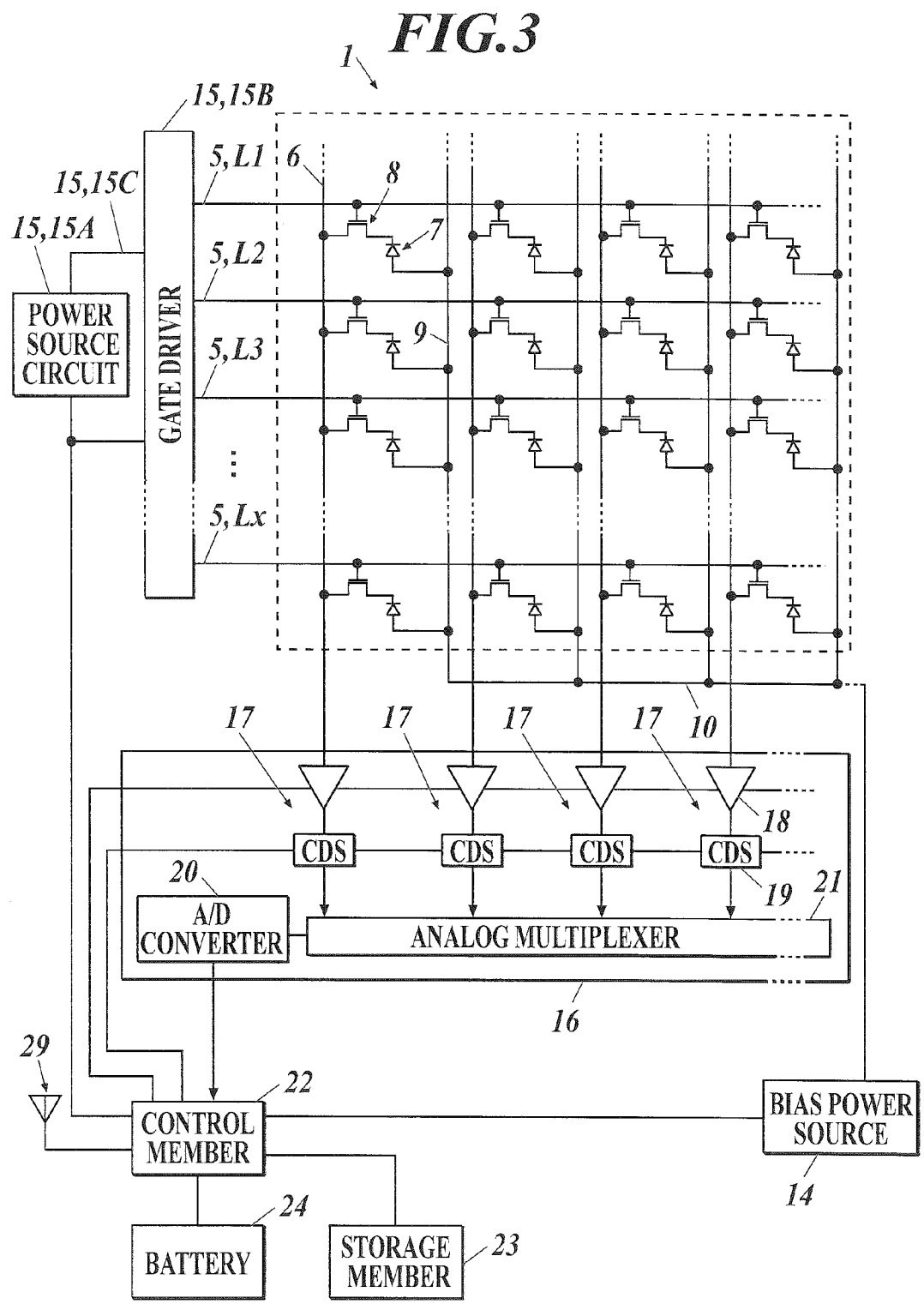
FIG. 3 is a block diagram illustrating an equivalent circuit of the FPD cassette.

FIG. 3 is a block diagram illustrating an equivalent circuit of the FPD cassette 1. As illustrated in FIG. 3, in the FPD cassette 1, a plurality of conversion elements 7 are arranged in a two dimensional matrix on a non-illustrated sensor substrate. Each of the conversion elements 7 generates electrical signals depending on radiation which has been emitted from the radiation generator 70 and has passed through a non-illustrated object.

The bias lines 9 are connected to the corresponding conversion elements 7, and the bias lines 9 are connected to a bias power source 14 via a wire connection 10. The bias power source 14 applies a reverse bias voltage to each of the conversion elements 7 via the bias lines 9, etc. The Thin Film Transistors (TFTs) 8 as switch elements are connected to the conversion elements 7, respectively, and the TFTs 8 are connected to the corresponding signal lines 6.

In a scan driving member 15, a power source circuit 15A supplies an ON voltage and OFF voltage to a gate driver 15B via a line 15C, and the gate driver 15B switches a voltage to be applied to each of lines L1 to Lx of scanning lines 5 between the ON voltage and OFF voltage.

Each of the TFTs 8 is turned to an ON state when the ON voltage is applied thereto via the corresponding scanning line 5, and thereby each of the conversion elements 7 conducts with the corresponding signal line 6 so that electrical signals in the conversion elements 7 are read out. Each of the TFTs 8 is turned to an OFF state when the OFF voltage is applied thereto via the corresponding scanning line 5, and thereby conduction between each of the conversion elements 7 and the corresponding signal line 6 is cut off.

A control member 22 is composed of a computer in which a non-illustrated Central Processing Unit (CPU), Read Only Memory (ROM), Random Access Memory (RAM), input/output interface, etc. are connected to a bus, or a Field Programmable Gate Array (FPGA), etc. Alternatively, the control member 22 may be composed of a dedicated control circuit.

To the control member 22, a storage member 23 including a Static RAM (SRAM) and/or Synchronous DRAM (SDRAM) is connected, and further the antenna device 29 enabling wireless communication with outside apparatuses/devices is connected. Additionally, a battery 24 which supplies necessary power to each of the functional sections such as the scan driving member 15, readout circuits 17, the storage member 23, the bias power source 14, etc. are connected to the control member 22.

In the embodiment, the control member 22 performs, as preprocessing for imaging, a resetting process of each of the conversion elements 7. Concretely, as illustrated in FIG. 4, the control member 22 causes the scan driving member 15 (see FIG. 3) to sequentially apply the ON voltage to lines L1 to Lx of the scanning lines 5 so as to make the TFTs 8 connected to the corresponding scanning lines 5 sequentially are turned to the ON state, and removes electrical charge from the conversion elements 7.

Then, when the console 50 transmits a later-described request signal to the FPD cassette 1 via the relay unit 60 (see FIG. 1), the control member 22 performs the resetting process of the conversion elements 7 being executed at that time until the scan driving member 15 applies the ON voltage to the last line Lx of the scanning lines 5, and transmits a completion signal indicating that preprocessing for imaging has been completed to the console 50 at completion of the resetting process of the conversion elements 7 corresponding to the last line Lx of the scanning signals 5. As for transmission/reception of signals, data, etc. among the devices via the relay unit 60 will be specifically described later.

Figure 4:
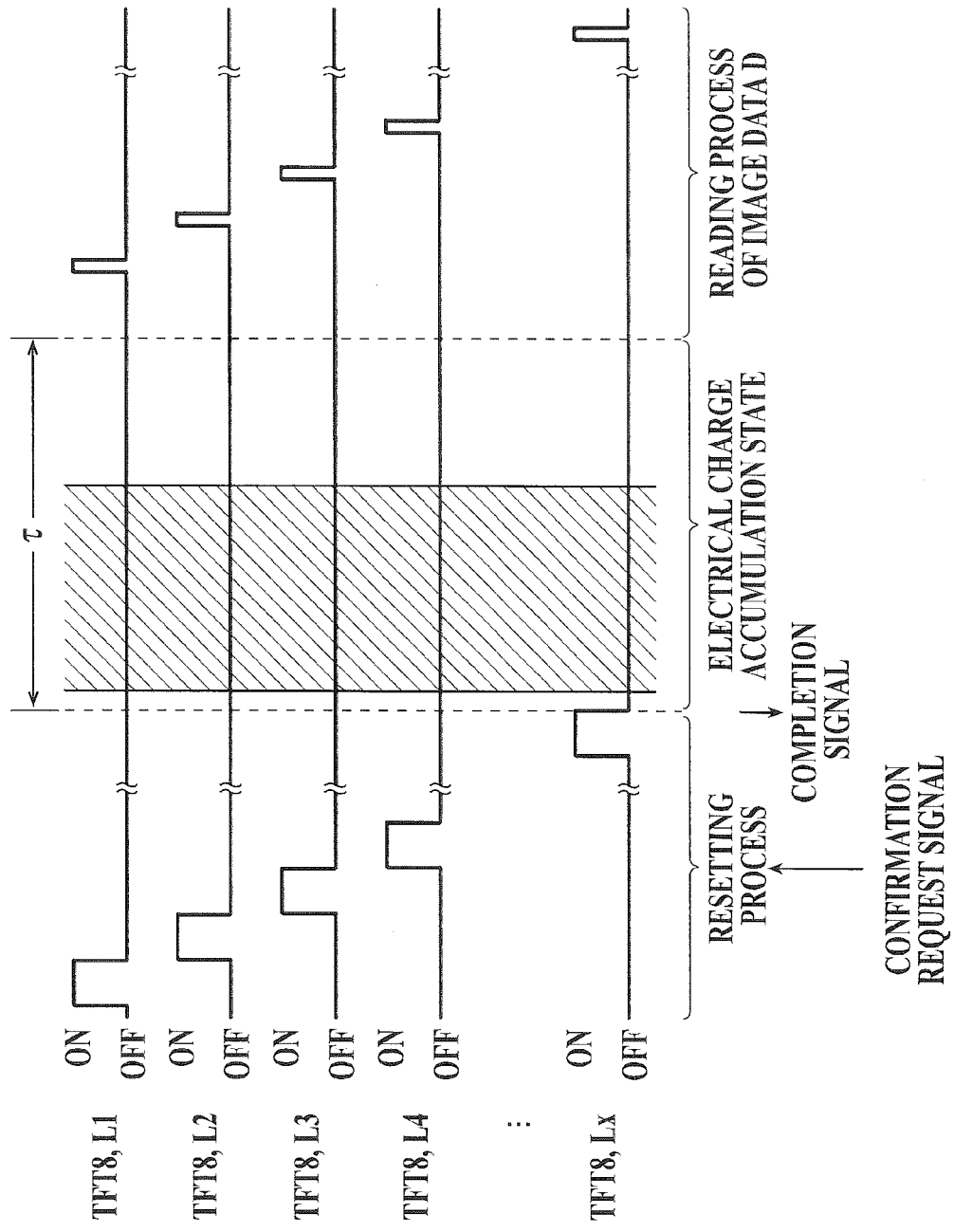
FIG. 4 is a timing chart for explaining timing of application of ON voltage to each scanning line when executing each process using the FPD cassette.

Then, as illustrated in FIG. 4, the control member 22 causes the scan driving member 15 to apply the OFF voltage to all lines L1 to Lx of the scanning lines 5 so that all of the TFTs 8 are turned to the OFF state, and causes the FPD cassette 1 to become an electrical charge accumulation state in which electrical charge is accumulated in the conversion elements 7, concurrently with the transmission of the completion signal. After that, during the electrical charge accumulation state of the FPD cassette 1, radiation is emitted. Incidentally, a shadow area in FIG. 4 represents a time period during which the radiation generator 70 (see FIG. 1) emits radiation.

The control member 22 makes the electrical charge accumulation state continued during a predetermined time period $\tau$ (hereinafter referred to as "accumulation time period $\tau$"), and then, as illustrated in FIG. 4, causes the scan driving member 15 to sequentially apply the ON voltage to each of lines L1 to Lx of the scanning lines 5 so as to perform a reading process of image data D from each of the conversion elements 7.

Concretely, when the scan driving member 15 applies the ON voltage to a certain scanning line 5, the TFTs 8 connected to the certain scanning line 5 are turned to the ON state. By this, each of the conversion elements 7 conducts with the corresponding signal line 6, and electrical charge (i.e. electrical signal) in each of the conversion elements 7 is read out by each of the readout circuits 17 included in a readout IC 16 (see FIG. 3). Specifically, each of amplifying circuits 18 of each of the readout circuits 17 outputs a voltage value depending on an amount of electrical charge flowing into each of the amplifying circuits 18.

Each of correlated doubling sampling circuits 19 (indicated as "CDSs" in FIG. 3) outputs a difference between voltage values which are output from each of the amplifying circuits 18 before and after flowing-in of electrical charge from each of the conversion elements 7, as a piece of image data D having an analog value, to the downstream side of each of the correlated doubling sampling circuits 19. The output image data D are sequentially transmitted to an A/D converter 20 via an analog multiplexer 21, converted into a piece of image data D having a digital value, and output to the storage member 23 to be stored therein. The reading process of image data D is thus performed.

Incidentally, when radiographic imaging is performed and image data D are read out from the conversion elements 7 as described above, the control member 22 extracts a specific ratio of the image data D each corresponding to one (1) frame, namely, corresponding to all conversion elements 7 connected to each scanning line 5, and transmits the extracted image data D, as a preview image signal, to the console 50 via the relay unit 60 (see FIG. 1).

Concurrently with the transmission of the preview image signal, the control member 22 repeats the processing sequence (i.e. applying the ON voltage to each of the scanning lines 5, etc.) from the resetting process of the conversion elements 7 to the reading process of the image data D through the electrical charge accumulation state illustrated in FIG. 4, also in the state that the radiation generator 70 does not emit radiation to the FPD cassette 1, so as to perform a reading process of offset data O corresponding to dark electrical charge generated in each of the conversion elements 7, instead of reading out the image data D.

When the reading process of offset data O is completed, the control member 22 subsequently transmits the image data D other than already-transmitted preview image signal, and/or the read-out offset data O to the console 50 via the relay unit 60.

[Console 50]

The console 50 (see FIG. 1) of the embodiment is composed of a general-purpose computer, but may also be composed of a dedicated device. Although FIG. 1 illustrates the example where the console 50 is a laptop personal computer, the console 50 may be composed of a portable terminal carried by a radiologist, etc. In either case, the console 50 of the embodiment is portable so as to be brought into an imaging location.

The console 50 basically has various functions as that used for general imaging and/or mobile X-ray imaging, for example, as the console described in Japanese Patent Application Laid-Open Publication No. 2012-105787.

The console 50 is equipped with a display section 51 composed of a Cathode Ray Tube (CRT) or a Liquid Crystal Display (LCD), and also equipped with an input member 52 such as a keyboard and a mouse.

The console 50 is also equipped with a wireless communication device 53 including an antenna etc., and is capable of performing transmission/reception of signals and the like to/from the relay unit 60 via the wireless communication device 53. Incidentally, transmission/reception of signals, data, etc. among the devices via the relay unit 60, including communication between the console 50 and the relay unit 60, will be specifically described later.

When the console 50 receives the preview image signal transmitted from the FPD cassette 1 via the relay unit 60 as described above, the console 50 performs simple image processing to the preview image signal so as to create a preview image P_PRE, and displays the created preview image P_PRE in the display section 51.

When the console 50 receives the image data D and/or the offset data O transmitted from the FPD cassette 1 via the relay unit 60 as described above, the console 50 performs precise image processing such as gain correction, defective pixel correction, gradation processing depending on an imaging region and/or an imaging object so as to create a radiographic image P, and displays the created radiographic image P in the display section 51.

In the embodiment, a radiologist or the like directly inputs the imaging order information, in which information of an imaging target (i.e. patient or animal) and/or information of imaging conditions are set with respect to radiographic imaging to be performed in an imaging location, by using the input member 52 of the console 50, before imaging. As necessary, the imaging order information can be previously obtained from a Hospital Information System (HIS) and/or a Radiology Information System (RIS) of facilities such as a hospital in wireless communication or wire communication.

When the created radiographic image P is approved by a radiologist or the like, the console 50 performs processing such as correlating the approved radiographic image P to the corresponding imaging order information and storing them therein.

In addition to the above, the console 50 can control the operation of the FPD cassette 1 by transmitting a wake-up signal to the FPD cassette 1 via the relay unit 60 so as to change an imaging mode of the FPD cassette 1 from a sleep mode in which power is supplied only to necessary functional sections such as the antenna device 29 (see FIG. 3) and radiographic imaging cannot be performed, to an imagable mode (also called as a wake-up mode, etc.) in which power is supplied to the respective functional sections such as the scan driving member 15 and the readout circuits 17 and radiographic imaging can be performed.

The console 50 may also have a configuration in which a tube voltage to be set in the radiation generator 70 or the like can be input thereto so that the tube voltage or the like is transmitted to the radiation generator 70 via the relay unit 60 and set therein.

[Relay Unit 60]

Next, the relay unit 60 (see FIG. 1) is composed of a computer or a dedicated device, which includes a first communication section 61 to execute wireless communication with the FPD cassette 1 and/or the console 50, and a second communication section 62 to execute wireless communication with the portable radiation generator 70 which emits radiation to an object. Also the relay unit 60 is portable so as to be brought into an imaging location similarly to the FPD cassette 1, the console 50 and the radiation generator 70.

In the embodiment, the first communication section 61 of the relay unit 60 performs wireless communication with the FPD cassette 1 and/or the console 50 by a wireless LAN system conforming to IEEE802.11 standard. The second communication section 62 of the relay unit 60 performs wireless communication with the radiation generator 70 by a Frequency Shift Keying (FSK) system in UHF band. The wireless communication by the first communication section 61 or the second communication section 62 can be performed by using other radio wave systems or optical systems such as infrared communication.

The relay unit 60 of the embodiment is equipped with a communication control member 63 to control the wireless communication by the first communication section 61 or the second communication section 62. The relay unit 60 further includes a non-illustrated converter to perform conversion from signals etc. used in LAN communication with the console 50 to signals etc. used in communication by the FSK system with the radiation generator 70, and vice versa.

The relay unit 60 further includes a judgment member 64 which judges whether or not wireless communication connection has been established between the relay unit 60 and the radiation generator 70 on the basis of whether or not the second communication section 62 of the relay unit 60 has received the signals etc. transmitted from the radiation generator 70. Incidentally, each of the communication control member 63, the judgment member 64, the first communication section 61 and the second communication section 62 is illustrated as independent member in FIG. 1, but it is a mere example in the case that they are classified on a function basis. The relay unit 60 may have any other device configurations as long as it has the functions of the above members and the communication sections.

The communication section does not have to be divided into the first communication section 61 and the second communication section 62 as described above. For example, it is also possible to switch the communication to be performed between the communication with the FPD cassette 1 and/or the console 50 and the communication with the radiation generator 70.

The communication control member 63 of the relay unit 60 normally performs system control on the assumption that the radiation generator 70 is not ready for imaging, when the judgment member 64 judges that wireless communication connection has not been established between the relay unit 60 and the radiation generator 70. Concretely, the communication control member 63 prohibits the radiation generator 70 from emitting radiation even if there is performed an operation to cause the radiation generator 70 to emit radiation.

However, the communication control member 63 allows the radiation generator 70 to emit radiation even if the judgment member 64 judges that the situation where the wireless communication connection is not established between the relay unit 60 and the radiation generator 70 has occurred, after the FPD cassette 1 terminates the resetting process of the conversion elements 7, shifts to the electrical charge accumulation state, and outputs the completion signal indicating that the preprocessing for imaging has been completed, and once the judgment member 64 of the relay unit 60 judges that the wireless communication connection with the radiation generator 70 has been established and preparation for imaging has been completed. This point will be specifically described later.

[Radiation Generator 70]

The radiation generator 70 used in the portable radiographic imaging system 100 (see FIG. 1) of the embodiment is a portable radiation generator. Incidentally, the radiation generator 70 etc. illustrated in FIG. 1 can be mounted on a non-illustrated wagon to be formed as the mobile X-ray imaging cart, as described above.

The radiation generator 70 is equipped with a radiation source which emits radiation so that it reaches an object, though illustration is omitted. As the radiation source, for example, a Coolidge X-ray source, a rotary anode X-ray source, etc., which are widely used in a medical front, can be used. The radiation generator 70 is also equipped with an exposure switch 71 which is operated by a radiologist or the like to instruct the radiation generator 70 to start radiation emission.

The exposure switch 71 can be operated in two stages. When a radiologist or the like executes, as a first stage operation, for example, a half press operation by pressing the button of the exposure switch 71 up to a half depth thereof, the radiation generator 70 is activated with rotation of the anode, etc.

When a radiologist or the like executes, as a second stage operation, for example, a full press operation by pressing the button of the exposure switch 71 all the way down, the radiation generator 70 causes the radiation source to emit radiation. Then, when a radiologist or the like stops pressing the button of the exposure switch 71, the radiation generator 70 ends radiation emission.

Incidentally, though it is possible to make the exposure switch 71 and the radiation generator 70 exchange signals and the like therebetween in wireless communication, this would cause the risk that radiation is wrongly emitted due to the influence of other wireless communication paths. For this reason, the exposure switch 71 and the radiation generator 70 preferably exchange signals and the like therebetween in wire communication.

[Configurations and Operations Specific to the Present Invention]

Next, the operations of the portable radiographic imaging system 100 of the embodiment will be described according to the flow of an actual radiographic imaging process. Also the unique configurations of the portable radiographic imaging system 100 of the present invention will be described.

[Correlation Among Devices of System with Respect to Wireless Communication]

As described above, a radiologist or the like directly inputs the imaging order information in the console 50 by the input member 52 prior to imaging. Moreover, the identification information (i.e. SSID in this case) of a non-illustrated access point, which is to be used, provided in the first communication section 61 of the relay unit 60 is input in the console 50 and/or the FPD cassette 1.

In the embodiment, in order to allow the FPD cassette 1 to wirelessly communicate with the specific relay unit 60, a so-called Dongle including SSID information correlated to the specific relay unit 60 is connected to the FPD cassette 1 so that the identification information (SSID) of the access point of the relay unit 60 is input in the FPD cassette 1.

Moreover, in the embodiment, in order to allow the console 50 to wirelessly communicate with the specific relay unit 60, for example, by using the Dongle used for inputting the SSID in the FPD cassette 1, and by connecting the Dongle including the SSID information correlated to the specific relay unit 60 to the console 50, the identification information (SSID) of the access point of the relay unit 60 is input in the console 50.

By such configuration, the FPD cassette 1 and the console 50 become capable of wirelessly communicating with the specific relay unit 60. It is also possible to temporarily connect the FPD cassette 1 and/or the console 50 to the relay unit 60 with a non-illustrated cable so that SSID can be input.

Incidentally, instead of using the Dongle to input the identification information (SSID) of the access point of the relay unit 60 in the FPD cassette 1 and/or the console 50, for example, a configuration where a radiologist or the like operates the input member 52 to input and set the identification information (SSID) of the access point of the relay unit 60 to be used, in the console 50, can be adopted.

There can also be adopted a configuration where the console 50 previously stores a table in which each number of the available relay unit 60 is correlated to each piece of the identification information (SSID) of the access point of the relay unit 60, and a list of the available relay units 60 is displayed in the display section 51 of the console 50 by the operation by a radiologist or the like before imaging so that a radiologist or the like selects the relay unit 60 to be used from the list. In such configuration, the console 50 can also refer to the table to identify the identification information (SSID) of the access point corresponding to the number of the selected relay unit 60 so that the identification information (SSID) of the relay unit 60 to be used is automatically set in the console 50.

Regarding the FPD cassette 1, for example, the FPD cassette 1 can be connected to the console 50 with the cable before imaging, as described above, so that the identification information (SSID) of the access point of the relay unit 60 is transmitted from the console 50 to the FPD cassette 1 and set therein.

Figure 5:
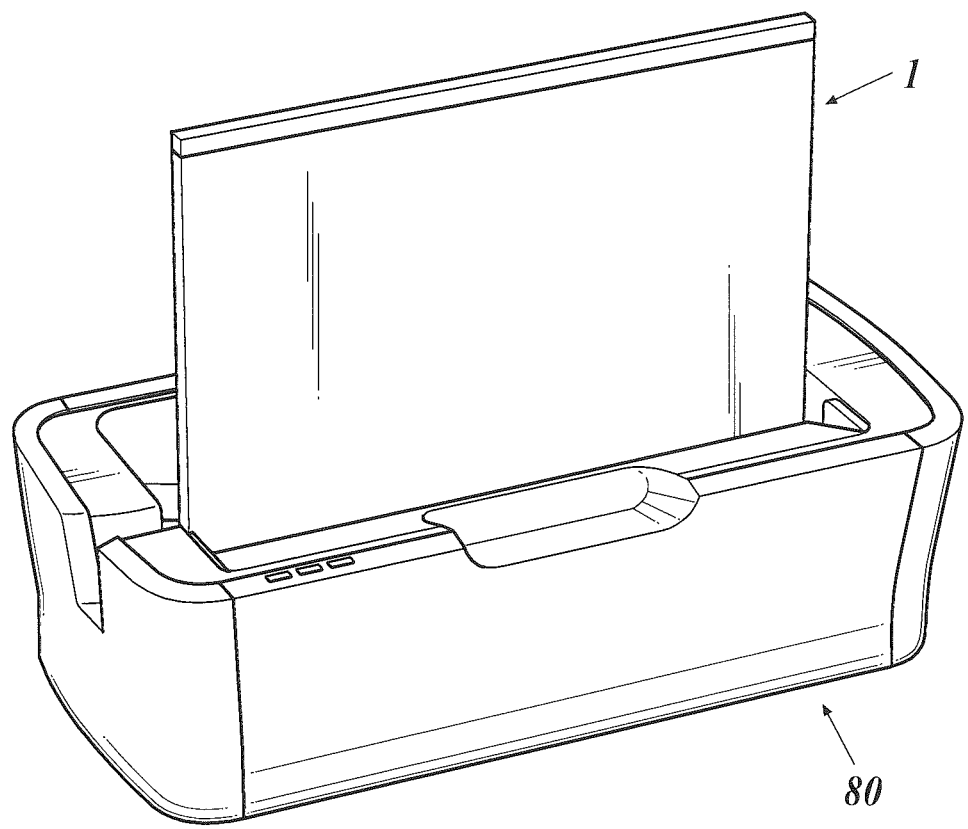
FIG. 5 is a diagram for explaining a configuration example of a cradle.

As a device which charges the battery 24 (see FIG. 3) of the FPD cassette 1, for example, a cradle 80 illustrated in FIG. 5 is sometimes used. The cradle 80 may be brought into an imaging location, and configured so that the identification information (SSID) of the access point of the relay unit 60 is input from the cradle 80 to the FPD cassette 1 and set therein when the FPD cassette 1 is mounted in the cradle 80.

Furthermore, a radiologist or the like can directly input and set, in the relay unit 60, the information such as the identification information, regarding wires communication, of the radiation generator 70 necessary for the relay unit 60 to execute wireless communication with the radiation generator 70. Such information can also be transmitted from the console 50 which has completed establishing wireless communication connection with the relay unit 60, as described above, to be set in the relay unit 60.

The above setting method is sufficient in the case that no imaging system is in operation therearound. However, the wireless communication connection between the radiation generator 70 and the relay unit 60 is preferably established by the following method, in view of the situation that a plurality of imaging systems are operational.

When a power source of the relay unit 60 is turned ON, the relay unit 60 shifts to a mode to receive an initial connection command for wireless communication setting, and maintains this mode while changing a reception frequency until the initial connection command is detected. When the initial connection command is not received within a predetermined time period, the relay unit 60 announces that fact as an error by sound or the like.

For example, there is considered the case that the radiation generator 70 sends out the initial command at 100 MHz. The relay unit 60 continuously changes the frequency such that the initial command is received for ten minutes at 10 MHz, for ten minutes at 20 MHz, for ten minutes at 30 MHz, and so on. In this case, the initial connection command is received at setting of 100 MHz. From that time, communication is executed only at 100 MHz, which is the frequency at the time of receiving the initial connection command.

When a power source of the radiation generator 70 is turned ON, the radiation generator 70 sends out the initial connection command at the frequency previously set for each radiation generator 70. Incidentally, in the case that another neighboring imaging system is in operation, the above frequency needs to be set to be different from a frequency band of the radiation generator 70 of the another imaging system, in order to prevent confusion among the systems.

The radiation generator 70, which has been newly operated, detects wireless communication around itself, and when recognizing the detected frequency band being currently used, may automatically set a frequency band separated from the currently-used frequency band by a predetermined band and then start transmitting of the initial connection command. Alternately, the currently-used radiation generator 70 may display the using frequency band so that a person such as a radiologist who operates the new radiation generator 70 can check it with eyes and manually sets the frequency.

Then, when the relay unit 60 receives the initial connection command, the relay unit 60 executes wireless communication with the radiation generator 70 at the frequency added to the initial connection command from that time. After that, the relay unit 60 replies to the radiation generator 70 to inform that the relay unit 60 has received the initial connection command, and the radiation generator 70 announces that it is being currently used (occupied), by an LED or the like.

Incidentally, when the power source of the radiation generator 70 is turned OFF and then turned ON again, the radiation generator 70 starts detecting wireless communication around it and transmitting the initial connection command. At that time, it is preferable to start automatic setting from the previous frequency band, which has been used until the power source is turned OFF. The power source is sometimes turned OFF once in order to cool the radiation generator 70. In such a case, the above setting is preferable because it enables restarting imaging promptly.

Moreover, when the power source of the relay unit 60 is turned OFF and then turned ON again, the relay unit 60 shifts to the mode to receive the initial connection command for wireless communication setting, and maintains this mode while changing the reception frequency until the initial connection command is detected. However, at that time, the radiation generator 70 has already terminated the mode in which the initial connection command is sent out.

However, the radiation generator 70 judges that the communication becomes unconnected, namely the wireless communication connection becomes unestablished, because the reply regarding wireless communication comes not to be obtained. When the communication is judged to be unconnected for a predetermined number of times, the radiation generator 70 restarts the mode, which is that at the time of activation, to detect the wireless communication therearound and transmit the initial connection command. By this restarting, the radiation generator 70 and the relay unit 60 are reconnected to each other, namely, wireless communication connection therebetween is established, in due course.

Incidentally, by making at least one of the radiation generator 70 and the relay unit 60 display the ID information and the like of a partner being paired therewith and used after establishing wireless communication connection between the relay unit 60 and the radiation generator 70, a person who perform imaging can recognize the device that the person himself/herself is currently using, in the case that a plurality of imaging system are in operation, which is preferable.

In the embodiment, each of the FPD cassette 1, the console 50 and the radiation generator 70 is thus configured to execute wireless communication with the relay unit 60. In other words, in the portable radiographic imaging system 100 (see FIG. 1) of the embodiment, each of the FPD cassette 1, the console 50 and the radiation generator 70 is correlated to the relay unit 60 on a one-to-one basis, with respect to wireless communication.

For example, when the console 50 is replaced with another console 50 in the portable radiographic imaging system 100 of the embodiment, by setting the identification information (SSID) of the access point of the relay unit 60 to the newly-replaced console 50 as described above, the newly-replaced console 50 becomes possible to wirelessly communicate with the relay unit 60.

To the relay unit 60, the FPD cassette 1 and the radiation generator 70 are already correlated, with respect to wireless communication. By this, the newly-replaced console 50 can wirelessly communicate with the FPD cassette 1 and/or the radiation generator 70 via the relay unit 60 in the portable radiographic imaging system 100 only by setting the identification information (SSID) of the access point of the relay unit 60 in the newly-replaced console 50.

Moreover, for example, also in the case that the battery of the FPD cassette 1 is dead and the another new FPD cassette 1 is incorporated in the portable radiographic imaging system 100, similarly to the above, the newly-incorporated FPD cassette 1 can wirelessly communicate with the console 50 and/or the radiation generator 70 via the relay unit 60 in the portable radiographic imaging system 100 only by setting the identification information (SSID) of the access point of the relay unit 60 to the newly-incorporated FPD cassette 1.

Thus, in the embodiment, only by setting the identification information (SSID in the case that the newly-incorporated device is the FPD cassette 1 and/or the console 50, and identification information regarding the wireless communication in the case that the newly-incorporated device is the radiation generator 70) of the access point of the relay unit 60 in the newly-replaced/incorporated device, when replacing the device of the system 100 with another device or incorporating a new device into the system 100, the newly replaced/incorporated device comes being into possible to wirelessly communicate with other devices in the portable radiographic imaging system 100.

As described above, in the portable radiographic imaging system 100 of the embodiment, it is not necessary to perform complicated setting process for setting the identification information or the like between the new device and the other devices, when replacing the device of the system with another device or incorporating the new device into the system. Only by setting the identification information or the like of the access point of the relay unit 60 to the new device, the new device can execute wireless communication with the other devices in the system.

By this, the system very easily comes into the state that the devices thereof can wirelessly communicate with one another even in the case of replacing the device of the system with another device and/or incorporating a new device into the system. In addition, it becomes possible to accurately prevent the situation that correlation regarding wireless communication among certain devices is forgot in the complicated setting process for setting the identification information of each device in another device among the new device and the other devices and accordingly imaging cannot be accurately executed.

In other words, in the portable radiographic imaging system 100 of the embodiment, by adopting the configuration where each of the FPD cassette 1, the console 50 and the radiation generator 70 is correlated to the relay unit 60 on a one-to-one basis with respect to wireless communication as described above, it is possible to easily and accurately make the state that the devices of the system can wirelessly communicate with one another.

[Transmission/Reception of Signals and the Like Among the Devices Via the Relay Unit]

Next, the transmission/reception of signals, data, etc. among the devices via the relay unit 60 in the portable radiographic imaging system 100 when performing imaging will be described.

The FPD cassette 1 of the embodiment executes the resetting process of the conversion elements 7, as the preprocessing for imaging, when a radiologist of the like turns on the power switch 25 (see FIG. 2), and/or when the FPD cassette 1 receives the wake-up signal transmitted from the console 50 and the imaging mode changes from the sleep mode to the imagable mode as described above.

Concretely, as described above, the control member 22 of the FPD cassette 1 repeatedly executes the resetting process of the conversion elements 7, in which the scan driving member 15 (see FIG. 3) sequentially applies the ON voltage to lines L1 to Lx of the scanning lines 5 as illustrated in the left-hand portion of FIG. 4.

Then, a radiologist or the like executes positioning of the FPD cassette 1 with respect to an object by putting the FPD cassette 1 to the object (including not only a patient but also a farm animal and/or an animal such as a racehorse). When the positioning is completed, the exposure switch 71 of the radiation generator 70 (see FIG. 1) is operated so that the radiation generator 70 emits radiation.

As described above, the exposure switch 71 of the radiation generator 70 can be operated in two stages. When a radiologist or the like performs, as the first stage operation, a half press operation of the exposure switch 71, the radiation generator 70 transmits a signal (hereinafter simply referred to as the first-stage operation signal) indicating that the first stage operation has been performed in the exposure switch 71, to the console 50 via the relay unit 60.

When the console 50 receives the first-stage operation signal from the radiation generator 70 via the relay unit 60, the console 50 transmits the request signal to the FPD cassette 1 to request it to terminate the resetting process of the conversion elements 7 and shift to the electrical charge accumulation state.

As described above, when the FPD cassette 1 receives the request signal transmitted from the console 50 via the relay unit 60, the control member 22 of the FPD cassette 1 executes the resetting process of the conversion elements 7 being performed at that time until the scan driving member 15 applies the ON voltage to the last line Lx of the scanning lines 5. When the resetting process of the conversion elements 7 corresponding to the last line Lx of the scanning line 5 is completed, the control member 22 of the FPD cassette 1 transmits the completion signal indicating that the preprocessing for imaging has been completed to the console 50 via the relay unit 60 (see FIG. 4).

Incidentally, as illustrated in FIG. 4, the control member 22 of the FPD cassette 1 causes the scan driving member 15 to apply the OFF voltage to all lines L1 to Lx of the scanning line 5, concurrently with the transmission of the completion signal, so that all of the TFTs 8 are turned to the OFF state and the FPD cassette 1 shifts to the electrical charge accumulation state, as described above.

When the console 50 receives the completion signal from the FPD cassette 1, the console 50 transmits a signal (hereinafter referred to as an interlock release signal) to allow the radiation generator 70 to emit radiation, to the radiation generator 70 via the relay unit 60. When the radiation generator 70 receives the interlock release signal transmitted from the console 50 via the relay unit 60, the radiation generator 70 transmits an emission start signal to the radiation source at the point of time when a radiologist or the like performs, as the second stage operation, the full press operation in the exposure switch 71, so that the radiation source emits radiation.

As illustrated in FIG. 4, the radiation generator 70 terminates radiation emission while the FPD cassette 1 is in the electrical charge accumulation state. The control member 22 of the FPD cassette 1 makes the electrical charge accumulation state continued during the predetermined time period τ, and then causes the scan driving member 15 to sequentially apply the ON voltage to lines L1 to Lx of the scanning lines 5 to read out the image data D from each of the conversion elements 7. Additionally, the control member 22 executes various processes as necessary. Thus radiographic imaging is performed.

In the above, the example where the console 50, that has received the signal from the radiation generator 70, transmits the signal to the FPD cassette 1, and the example where the console 50, that has received the signal from the FPD cassette 1, transmits the signal to the radiation generator 70 are described. However, there may be a configuration where the radiation generator 70 and the FPD cassette 1 directly (without interposing the console 50) exchange the signals to each other via the relay unit 60.

[Processing 1 in the Case that Wireless Communication Connection with the Radiation Generator is not Established]

Meanwhile, in the embodiment, the communication control member 63 (see FIG. 1) of the relay unit 60 is configured to cause the second communication section 62 to periodically transmit a confirmation signal to the radiation generator 70.

The judgment member 64 of the replay unit 60 then judges whether or not wireless communication connection with the radiation generator 70 has been precisely established on the basis of whether or not the second communication section 62 of the relay unit 60 receives a response signal as a response to the confirmation signal from the radiation generator 70, as described above.

Concretely, for example, the judgment member 64 of the relay unit 60 is configured to judge that the wireless communication connection with the radiation generator 70 has not been established when the response signal is not received from the radiation generator 70 within a predetermined time period T after the relay unit 60 transmits the confirmation signal to the radiation generator 70.

Not only in the case that the response signal is never received from the radiation generator 70 after the relay unit 60 transmits the confirmation signal to the radiation generator 70, but also in the case that the time period from the transmission of the confirmation signal to the reception of the response signal from the radiation generator 70 is unduly long, it cannot be said that the system is in the environment where wireless communication can be accurately performed.

For this reason, by configuring the system so that it is judged that wireless communication connection with the radiation generator 70 is not established when the response signal is not received from the radiation generator 70 within the predetermined time period T, it becomes possible to judge that wireless communication connection with the radiation generator 70 has been established only when the relay unit 60 and the radiation generator 70 are in the state that they can accurately execute wireless communication with each other. By this, the relay unit 60 and the radiation generator 70 become capable of accurately executing wireless communication with each other, or in the situation that accurate wireless communication is impossible, the system can accurately judge that wireless communication connection has not been established.

Incidentally, the judgment member 64 of the relay unit 60 can also be configured to judge that wireless communication connection with the radiation generator 70 has not been established when the reception condition of the response signal is very poor though the response signal has been received from the radiation generator 70, for example, when the magnitude of the received response signal is very small and there is a possibility that wireless communication connection would be disconnected.

When the judgment member 64 judges that wireless communication connection with the radiation generator 70 has not been established, the communication control member 63 of the relay unit 60 normally prohibits the radiation generator 70 from emitting radiation even when the operation to make radiation emitted is performed in the radiation generator 70.

Concretely, there is considered, for example, the case that the exposure switch 71 of the radiation generator 70 is half-pressed so that the relay unit 60 transfers the first-stage operation signal from the radiation generator 70 to the console 50, and then the judgment member 64 judges that wireless communication connection with the radiation generator 70 has not been established, for example, because the response signal is not received, in response to the confirmation signal periodically transmitted to the radiation generator 70, for some reason within the predetermined time period T.

In this case, the communication control member 63 of the relay unit 60 executes the above normal processing. Concretely, though the console 50 (or the FPD cassette 1 in the case that the FPD cassette 1 and the radiation generator 70 directly exchange the signals to each other) that has received the completion signal from the FPD cassette 1 transmits the interlock release signal to the relay unit 60 and requests it to transfer the signal to the radiation generator 70, the communication control member 63 of the relay unit 60 does not transfer the interlock release signal to the radiation generator 70.

In this case, even when a radiologist or the like executes the full press operation, which is the second state operation, the radiation generator 70 does not emit radiation because it has not received the interlock release signal.

The communication control member 63 of the relay unit 60 prohibits the radiation generator 70 from emitting radiation even when the operation (i.e. the half press operation in this case) to allow the radiation generator 70 to emit radiation is executed, when the judgment member 64 judges that wireless communication connection with the radiation generator 70 has not been established, for example, by the way described above, namely, by not transferring the interlock release signal transmitted from the console 50 (or the FPD cassette 1; the same shall apply hereinafter) to the radiation generator 70 which is in the interlock state.

In the above case, the response signal is not sent from the radiation generator 70 in response to the confirmation signal periodically transmitted from the relay unit 60 within the predetermined time period T, or alternatively, the magnitude of the response signal becomes very small, though the cause thereof is unknown. In such a state, even if the interlock release signal transmitted from the console 50 is transferred to the radiation generator 70, there is a possibility that the radiation generator 70 cannot receive the interlock release signal. In the case that the radiation generator 70 cannot receive the interlock release signal, the radiation generator 70 will never emit radiation.

On the other hand, the FPD cassette 1 automatically starts the reading process of the image data D when the preprocessing for imaging, namely, the resetting process (see FIG. 4) of the conversion elements 7 is completed, the FPD cassette 1 shifts to the electrical charge accumulation state, and the predetermined accumulation time period $\tau$ has elapsed. However, when the image data D is read out in such a state, only the image data D which does not include a photograph of an object is obtained. This results in totally useless processing by the FPD cassette 1, and accordingly the power of the battery 24 (see FIG. 3) of the FPD cassette 1 is wastefully consumed.

Incidentally, when the power of the battery 24 of the FPD cassette 1 is thus wastefully consumed, the number of the radiographic images that can be taken by one time electrical charging of the battery 24 decreases, and imaging efficiency by one time electrical charging lowers. The battery therefore needs to be frequently charged, for example, by using the cradle illustrated in FIG. 5, and this causes the problem that work efficiency of radiographic imaging lowers.

For this reason, in the embodiment, when the system is in the situation that possibly causes the above problem, namely, the situation that the radiation generator 70 does not respond to the confirmation signal periodically transmitted from the relay unit 60 within the predetermined time period T, and when the judgment member 64 judges that wireless communication connection with the radiation generator 70 has not been established, the radiation generator 70 is prohibited from emitting radiation even when a radiologist or the like operates the radiation generator 70 so that it emits radiation.

By configuring the system as described above, the situation that the signal is transmitted or received for executing radiographic imaging in the situation that it is judged that wireless communication connection has not been established at least between the relay unit 60 and the radiation generator 70, the signal transmitted from one device cannot be received accurately by another device, and radiographic imaging cannot be performed, can be accurately prevented.

As described above, if a patient brings the portable radiographic imaging system 1 into his/her home, there is a possibility the situation that wireless communication connection is not established occurs. Concretely, there may be a situation where communication environment is deteriorated due to wireless communication established among various apparatuses/devices other than the system 1 in the imaging location, and accordingly wireless communication connection between the relay unit 60 and the radiation generator 70 is disconnected in the portable radiographic imaging system 1.

Moreover, in the case that a farm animal such as a cow and/or an animal such as a racehorse breaks a bone, and/or in the case of performing radiographic imaging of teeth of a dead body for a body identification in time of disaster, there may be a situation where a plurality of portable radiographic imaging systems 1 are brought into an imaging location and radio waves used in wireless communication of the plural systems 1 fly about in one (1) imaging location, which is so-called busy state of communication.

In the above situation, it takes time for the relay unit 60 or the radiation generator 70 to perform processing to judge whether or not received signals, data, etc. are those that are to be transmitted to the relay unit 60 or the radiation generator 70 itself in order to avoid confusion. Therefore, there may a situation where the judgment member 64 of the relay unit 60 judges that wireless communication connection with the radiation generator 70 has not been established, for example, when the radiation generator 70 cannot transmit the response signal in response to the confirmation signal periodically transmitted from the relay unit 60 within the predetermined time period T.

Even if the replay unit 60 transfers the interlock release signal, which has been transmitted from the console 50, to the radiation generator 70 to allow the radiation generator 70 to emit radiation in such a situation, there is a possibility that the trouble that the interlock release signal is not transmitted to the radiation generator 70 occurs and radiographic imaging cannot be executed accurately.

For this reason, by prohibiting the radiation generator 70 from emitting radiation when the judgment member 64 of the relay unit 60 judges that wireless communication connection with the radiation generator 70 has not been established, the above trouble can be accurately prevented from occurring.

Incidentally, in the case of configuring the system as described above, the relay unit 60 preferably transmits a signal to instruct the FPD cassette 1 to stop continuing the electrical charge accumulation state and execute the preprocessing for imaging, namely, the resetting process of the conversion elements 7, to the FPD cassette 1 directly or via the console 50, for example, when the console 50 transmits the interlock release signal to the relay unit 60 through the above process in the state that the judgment member 64 of the relay unit 60 judges that wireless communication connection with the radiation generator 70 has not been established and the communication control member 63 of the relay unit 60 prohibits the radiation generator 70 from emitting radiation.

The relay unit 60 is preferably configured to cause, when the judgment member 64 judges that wireless communication connection with the radiation generator 70 has not been established as described above, the console 50 and/or the FPD cassette 1 to announce that wireless communication connection has not been established between the relay unit 60 and the radiation generator 70, at that time, regardless of transmission of the interlock release signal and the like.

By configuring the system as described above, the FPD cassette 1 can be prevented from wastefully shifting to the electrical charge accumulation state or executing the reading process of the image data D in the state that the radiation generator 70 is prohibited from emitting radiation, and thereby the power of the battery 24 can be accurately prevented from being wastefully consumed.

Incidentally, the prohibition state of radiation emission of the radiation generator 70 is cleared when the judgment member 64 judges that wireless communication connection with the radiation generator 70 has been established because the relay unit 60 receives the response signal from the radiation generator 70 within the predetermined time period T again in response to the confirmation signal transmitted from the relay unit 60 to the radiation generator 70, after the judgment member 64 judges that wireless communication connection with the radiation generator 70 has not been established and the radiation generator 70 is prohibited from emitting radiation.

[Processing 2 in the Case that Wireless Communication Connection with the Radiation Generator is not Established]

In the embodiment, when a radiologist or the like executes the half press operation of the exposure switch 71 of the radiation generator 70 as described above, the relay unit 60 transfers the first-stage operation signal from the radiation generator 70 to the console 50, transfers the request signal (i.e. the request signal to request to terminate the resetting process of the conversion elements 7 and shift to the electrical charge accumulation state, as described above) from the console 50 to the FPD cassette 1, and transfers the completion signal indicating that the preprocessing for imaging has been completed, from the FPD cassette 1 to the console 50.

In the above example, when the judgment member 64 of the relay unit 60 judges that wireless communication connection with the radiation generator 70 has not been established before the relay unit 60 transfer the interlock release signal to the radiation generator 70, the interlock release signal having been transmitted from the console 50 on the basis of the completion signal from the FPD cassette 1, the relay unit 60 prohibits the radiation generator 70 from emitting radiation, by the method such as not transferring the interlock release signal to the radiation generator 70.

Meanwhile, there may be a case where the judgment member 64 of the relay unit 60 judges that wireless communication connection with the radiation generator 70 has not been established, after the relay unit 60 transfers the interlock release signal transmitted from the console 50 to the radiation generator 70. Concretely, for example, there may be a case where the radiation generator 70 does not transmit the response signal in response to the confirmation signal periodically transmitted from the relay unit 60 within the predetermined time period T, immediately after the interlock release signal from the console 50 is transferred to the radiation generator 70.

If the radiation generator 70 is prohibited from emitting radiation as described above in such a case, imaging is stopped though the FPD cassette 1 has completed the preprocessing for imaging and is in the state capable of capturing the image data D by emitting radiation. Thus, though both of the FPD cassette 1 and the radiation generator 70 are in the state capable of performing radiographic imaging, radiographic imaging is not performed in the result, and a good opportunity for imaging is lost.

Thus, when the radiation generator 70 is prohibited from emitting radiation in this case, a good opportunity for imaging is wasted after all, contrary to the above case. The FPD cassette 1 needs to execute the preprocessing for imaging again and the power of the battery 24 is wastefully consumed, and thereby the problem described above occurs.

To solve this problem, in this embodiment, the relay unit 60 ignores the judgment by the judgment member 64 and allows the radiation generator 70 to emit radiation, when the judgment member 64 of the relay unit 60 judges that wireless communication connection with the radiation generator 70 has not been established, after the FPD cassette 1 sends the completion signal indicating that the preprocessing for imaging has been completed, the console 50 that has received the completion signal sends the interlock release signal, and the interlock release signal is transferred to the radiation generator 70.

In the above case, when the judgment member 64 judges that wireless communication connection with the radiation generator 70 has not been established before receiving the interlock release signal from the console 50, the relay unit 60 prohibits the radiation generator 70 from emitting radiation. However, when the judgment member 64 makes the same judgment after receiving the interlock release signal from the console 50, the relay unit 60 allows the radiation generator 70 to emit radiation.

The radiation generator 70 can emit radiation to the FPD cassette 1 through an object so that radiographic imaging is accurately performed even in the state that wireless communication connection has not been established between the relay unit 60 and the radiation generator 70, when the FPD cassette 1 completes the preprocessing for imaging and is in the state capable of accurately obtaining the image data D by emitting radiation, and when the radiation generator 70 receives the interlock release signal so that the interlock state thereof is released and is in the state capable of emitting radiation.

By such configuration, even in the case that the system is put into the state where the relay unit 60 and the radiation generator 70 cannot wirelessly communicate with each other after the relay unit 60 transfers the interlock release signal to the radiation generator 70 and the FPD cassette 1 and the radiation generator 70 are ready for imaging, by allowing the radiation generator 70 to emit radiation to perform radiographic imaging, the FPD cassette 1 can execute radiographic imaging accurately so that the image data D including a photograph of an object is read out.

Thus, the situation that imaging is wastefully prohibited though the system is capable of executing imaging, and that the power of the battery 24 of the FPD cassette 1 is wastefully consumed in order to return to the state to execute the preprocessing for imaging again, can be prohibited from occurring.

By this, it becomes possible to increase the number of the radiographic images that can be taken by one time electrical charging of the battery 24 of the FPD cassette 1, and thereby imaging efficiency by one time electrical charging can be improved. There is also the advantage that work efficiency of radiographic imaging is improved because the number of times to charge the battery 24 of the FPD cassette 1 is decreased.

[Advantages]

As described above, according to the portable radiographic imaging system 1 of the embodiment, each of the FPD cassette 1, the console 50 and the radiation generator 70 is correlated to the relay unit 60 on a one-to-one basis with respect to wireless communication.

By this, it becomes unnecessary to perform the complicated setting process such as setting each piece of the identification information (SSID in the case that the newly-incorporated device is the FPD cassette 1 or the console 50; identification information regarding wireless communication in the case that the newly-incorporated device is the radiation generator 70) of a device in another device among the new device and the existing devices of the system 1, when replacing the device of the system with another device or incorporating a new device in the system 1. By establishing wireless communication connection between the new device and the relay unit 60, the system can be easily put into the state the devices thereof can wirelessly communicate with one another.

It also becomes possible to prevent the situation that correlation regarding wireless communication among certain devices is forgot in the complicated setting process for setting each piece of the identification information of a device in another device among the new device and the existing devices of the system and accordingly imaging cannot be accurately executed. Thus, the system can be accurately put into the state where the devices thereof can wirelessly communicate with one another.

Meanwhile, according to the portable radiographic imaging system 1 of the embodiment, the relay unit 60 is configured to prohibit the radiation generator 70 from emitting radiation when the judgment member 64 judges that wireless communication connection with the radiation generator 70 has not been established.

Even when the relay unit 60 transfers the interlock release signal to the radiation generator 70, the interlock release signal allowing the radiation generator 70 to emit radiation, in the state that the relay unit 60 and the radiation generator 70 cannot wirelessly communicate with each other, there is a possibility that the interlock release signal is not transmitted to the radiation generator 70 and radiographic imaging is not accurately performed. However, by configuring the system as described above, it becomes possible to properly prevent the radiographic imaging from being executed when there is a possibility that imaging is not executed accurately. Thus, the above-described problem can be prevented accurately.

Moreover, according to the portable radiographic imaging system 1 of the embodiment, the radiation generator 70 is allowed to emit radiation when the judgment member 64 judges that wireless communication connection with the radiation generator 70 has not been established after the interlock release signal, which has been sent from the console 60 or the FPD cassette 1, is transferred to the radiation generator 70.

By this, contrary to the above, the radiation generator 70 is allowed to emit radiation even when the judgment member 64 of the relay unit 60 judges that wireless communication connection with the radiation generator 70 has not been established, in the case that the relay unit 60 transfers the interlock release signal to the radiation generator 70 and both of the FPD cassette 1 and the radiation generator 70 are in the state capable of performing radiographic imaging.

Accordingly, imaging can be performed accurately in the state that radiographic imaging can be executed accurately even in the case that wireless communication among the devices of the system 1 is disconnected. It is also possible to prevent the situation that imaging is wastefully prohibited though the system is in the state capable of executing imaging, and that the power of the battery 24 of the FPD cassette 1 is wastefully consumed.

[Variation]

Incidentally, as the above-described predetermined time period T which is used in the judging process by the judgment member 64 of the relay unit 60, namely, as the predetermined time period T used to judge whether or not the relay unit 60 receives the response signal from the radiation generator 70 within the predetermined time period T starting from transmission of the confirmation signal from the relay unit 60 to the radiation generator 70, a plurality of kinds of time periods can be set instead of using one (1) kind of fixed time period.

In the case of setting the plural time periods T, the system can be configured so that a radiologist or the like can input or select the predetermined time periods T in the console 50 and/or the radiation generator 70 so that the input/selected time periods T are transmitted to the relay unit 60 to be set therein.

Moreover, though there is no problem when the radiation generator 70 terminates radiation emission within the duration time of the electrical charge accumulation state (see FIG. 4), namely, within the accumulation time period τ in the above case, if the radiation emission is not terminated within the accumulation time period τ and continued up to and after the start of the reading process of the image data D, the read-out image data D would become unexpected values.

To avoid such situation, in the case that the plurality of kinds of predetermined time periods T can be set, an upper limit of the radiation emission time to be set in the radiation generator 70 may be set to a time period corresponding to a difference between the accumulation time period τ in the FPD cassette 1 and the above-described predetermined time period T.

For example, when considering the case that the accumulation time period τ in the FPD cassette 1 is three seconds and the predetermined time periods T can be set to 200, 500 and 1000 milliseconds, the radiation emission time to be set in the radiation generator 70 is restricted to: a time less than 2.8 seconds in the case that the predetermined time period T is 200 milliseconds; a time less than 2.5 seconds in the case that the predetermined time period T is 500 milliseconds; and a time less than 2 seconds in the case that the predetermined time period T is 1000 milliseconds.

By configuring the system as described above, the radiation emission by the radiation generator 70 can be terminated within the accumulation time period τ in the FPD cassette 1, and radiographic imaging can be executed accurately because the radiation generator 70 does not emit radiation to the FPD cassette 1 during the reading process of the image data D.

Incidentally, it is needless to say that the present invention is not limited to the above embodiments and variations, and can be arbitrary changed without departing from the spirit of the present invention.

What is claimed is:

1. A portable radiographic imaging system, comprising:
   an FPD cassette;
   a portable console;
   a portable radiation generator; and
   a portable relay unit which performs wireless communication with the portable radiation generator emitting radiation to an object, wherein:
   each of the FPD cassette and the portable console is configured to perform wireless communication with the portable relay unit, and
   the portable relay unit prohibits the portable radiation generator from emitting radiation when judging that a wireless communication has not been established between the portable relay unit and the portable radiation generator, and allows the portable radiation generator to emit radiation when judging that the wireless communication has not been established between the portable relay unit and the portable radiation generator after the portable relay unit transfers to the portable radiation generator a signal to allow the portable radiation generator to emit radiation, the signal being sent from the FPD cassette or the portable console.

2. The portable radiographic imaging system of claim 1, wherein the portable relay unit judges that the wireless communication connection has not been established between the portable relay unit and the portable radiation generator when the portable relay unit does not receive a signal from the portable radiation generator within a predetermined time period after the portable relay unit transmits a signal to the portable radiation generator.

3. The portable radiographic imaging system of claim 2, wherein a plurality of time periods can be set as the predetermined time period.

4. The portable radiographic imaging system of claim 1, wherein the portable relay unit periodically performs a judging process to judge whether or not the wireless communication connection has been established between the portable relay unit and the portable radiation generator, and
   the portable relay unit causes the portable console and/or the FPD cassette to announce that the wireless communication connection has not been established between the portable relay unit and the portable radiation generator when judging that the wireless communication connection has not been established between the portable relay unit and the portable radiation generator.

5. The portable radiographic imaging system of claim 1, wherein the portable relay unit transmits a signal to instruct to stop currently-performed processing and return to a state to perform preprocessing for imaging, to the FPD cassette, when the signal to allow the portable radiation generator to emit radiation is transmitted from the FPD cassette or the portable console to the portable relay unit in the state that the portable radiation generator is prohibited from emitting radiation.

6. A radiographic imaging system, comprising:
   a plurality of portable radiographic imaging systems, wherein each portable radiographic imaging system of the plurality of radiographic imaging systems comprises:
   an FPD cassette;
   a portable console;
   a portable radiation generator: and
   a portable relay unit which performs wireless communication with the portable radiation generator emitting radiation to an object, wherein:
   each of the FPD cassette and the portable console is configured to perform wireless communication with the portable relay unit, and
   the portable relay unit prohibits the portable radiation generator from emitting radiation when judging that a wireless communication connection has not been established between the portable relay unit and the portable radiation generator, and allows the portable radiation generator to emit radiation when judging that the wireless communication connection has not been established between the portable relay unit and the portable radiation generator after the portable relay unit transfers to the portable radiation generator a signal to allow the portable radiation generator to emit radiation, the signal being sent from the FPD cassette or the portable console.

* * * * *